United States Patent [19]

Barouk et al.

[11] Patent Number: 4,546,557
[45] Date of Patent: Oct. 15, 1985

[54] SHOE, MORE ESPECIALLY FOR PATIENTS HAVING UNDERGONE A SURGICAL OPERATION ON THE FORE-FOOT

[75] Inventors: Louis S. Barouk, Yvrac; Maurice P. Mayzaud, Brive, both of France

[73] Assignee: Etablissements Mayzaud Maurice, Brive, France; by said Maurice P. Mayzaud

[21] Appl. No.: 503,143

[22] PCT Filed: Oct. 8, 1982

[86] PCT No.: PCT/FR82/00164
§ 371 Date: Jun. 8, 1983
§ 102(e) Date: Jun. 8, 1983

[30] Foreign Application Priority Data

Oct. 9, 1981 [FR] France ............................ 81 19104

[51] Int. Cl.[4] .................... A61F 5/00; A43B 21/00
[52] U.S. Cl. ................................... 36/110; 36/81; 36/11.5; 128/83.5; 128/83
[58] Field of Search ............. 128/581, 583, 584, 585, 128/596, 614, 83, 83.5, 166, 166.5; 36/81, 110, 11.5

[56] References Cited

U.S. PATENT DOCUMENTS

| 2,509,821 | 5/1950 | Holstrom | 36/81 |
| 2,725,648 | 12/1955 | Kirk et al. | 128/83.5 |
| 3,421,517 | 1/1969 | Sabel | 128/583 |
| 3,584,402 | 6/1971 | Silverman | 36/11.5 |
| 3,905,135 | 9/1975 | Debusk | 36/110 |
| 4,178,703 | 12/1979 | Pols | 36/110 |
| 4,446,856 | 5/1984 | Jordan | 128/83.5 |

FOREIGN PATENT DOCUMENTS 2097294 2/1972 France ........................ 36/110

Primary Examiner—Werner H. Schroeder
Assistant Examiner—Steven N. Meyers

[57] ABSTRACT

A shoe, more especially for patients having undergone a surgical operation on the fore-foot.

It comprises an upper (1) open at the front, this upper being formed from two quarters (2) for wrapping round the rear part of the patient's foot and an inner sole (3) resting on a thick sole (4), substantially higher at the front than at the back.

10 Claims, 1 Drawing Figure

U.S. Patent  Oct. 15, 1985  4,546,557
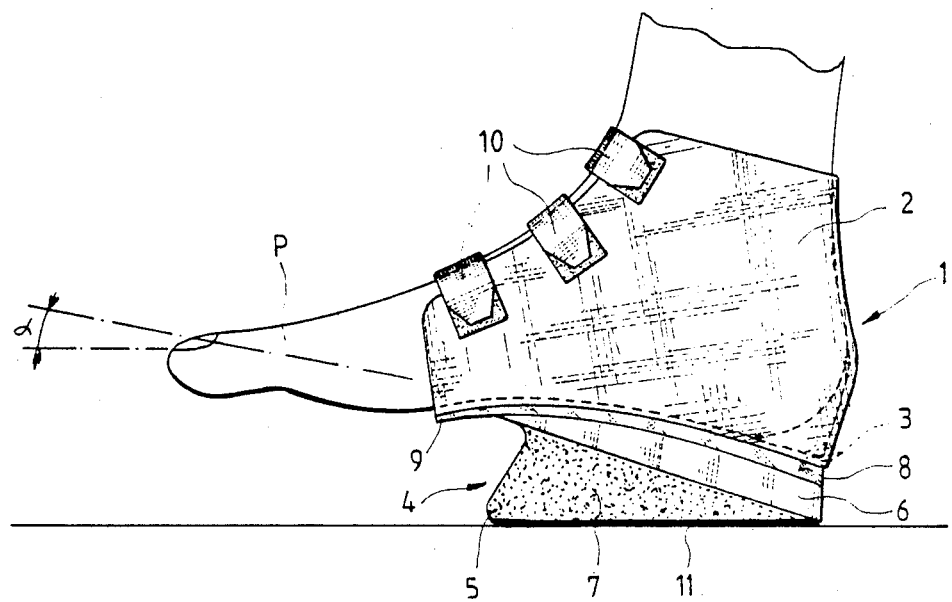

SHOE, MORE ESPECIALLY FOR PATIENTS HAVING UNDERGONE A SURGICAL OPERATION ON THE FORE-FOOT

The present invention relates to a shoe, more especially used as a post-operative shoe by convalescent patients who have undergone a surgical operation on the fore-foot (front part of the foot or metatarsus).

It is known that surgical operations on the fore-foot, which represent more than 75% of the operations carried out by foot surgeons, compel the patients not to put their weight on the operated fore-foot, at least during the first month of convalescence. On the other hand, the back part of the foot which is not painful may serve perfectly well as support point. All persons stricken with any affection of the fore-foot, not necessarily following a surgical operation, are moreover faced with this problem.

To resolve it, several possibilities are offered. One of them consists in not using the operated foot or the foot suffering from an affection at all and in walking with the help of sticks or crutches while putting one's weight on the other foot. Needless to say, this way of walking is very constraining and uncomfortable.

A second possibility consists quite simply in walking on the heel of the operated foot or the foot suffering from an affection, possibly by means of a molded plaster. In this case also, the walking position is very uncomfortable and may cause a lack of balance particularly with older people.

The difficulty of moving is aggravated when the surgical operation or the affection involves both feet.

The present invention proposes remedying these drawbacks and for this it provides a shoe, and more especially, a post-operative shoe which is characterized in that it comprises an upper open at the front, this upper being formed of two quarters for wrapping round the back part of the patient's foot and an inner sole resting on a sole substantially higher at the front than at the rear and this for example by about 1.5 cm.

With the particular structure of the upper of this shoe, the fore-foot extends completely outside the shoe which, because of the form of the sole, thicker at the front, holds the foot slightly sloping. Consequently, the operated forefoot or foot suffering from an infection is not subjected to any stress or strain caused by the shoe and, moreover, cannot come to bear on the ground during walking.

The front part of the sole may be shaped like a shock-absorbing wedge directed towards the front of the shoe. With this arrangement, the seating and the flexibility of the shoe is increased which confers on the patient a good balance while walking.

According to an important feature of the invention, the sole is compressible and has a degree of compressibility increasing from the rear to the front of the sole. To this end, the sole comprises a hard pad on which the inner sole of the upper rests, the remaining part of the sole being made from an homogeneous compressible material, such as a synthetic cellular foam, latex or rubber.

Preferably, the pad and the compressible part of the sole are integrally molded. Furthermore, the sole carries on its walking surface a protection plate made of a hard material.

Because of the variable compressibility of sole 4, sudden stopping of the support of the rear part of the foot at the level of the front part of the shoe is avoided, which considerably improves the comfort of the patient when walking. Furthermore, the pad serves as an anti-shock protection for the foot.

According to another important feature of the invention, a base is placed between the sole and the inner sole of the upper, this base extending beyond the front edge of this latter by a flexible downwardly curved tongue, which stops along a curve corresponding to the Lisfranc interline of the patient's foot. This tongue allows partial folding of the foot during walking while leaving the metatarsian structure free.

Advantageously, the quarters of the upper are made from strong cloth and are of sufficient height to wrap round the rear part of the patient's foot to above the peroneo-tibial malleoli. The upper thus holds the patient's foot perfectly in position to participate efficiently in the sloping positioning thereof.

Preferably, the two quarters of the upper may be connected together by self-gripping fasteners which allow adjustment of the closure of the upper depending on the size of the foot and more especially adjustment in time depending on the development of the post-operative oedema in the case of an operation on the fore-foot.

One embodiment of the present invention will be described hereafter by way of non limiting example with reference to the single FIGURE of the accompanying drawing which shows, in a side view, a post-operative shoe in accordance with the invention in position about the foot of the patient.

As can be seen, this shoe comprises an upper 1 open at the front, which is formed from two lateral quarters 2, only one of which can be seen in the FIGURE, and an inner sole 3 resting on a thick sole 4, substantially higher at the front than at the rear. The quarters 2 may be tightly connected together over the instep of the foot P so as to perfectly wrap round the rear part thereof.

Because of this particular structure, the shoe of the invention exerts no stress on the fore-foot and holds the foot P slightly sloping as represented by the angle α. Thus, the fore-foot suffering from a painful affection or just having been operated on, does not risk coming into contact with the ground during walking.

It will be noted that the front part of sole 4 is shaped like a shock-absorbing wedge 5 directed towards the front of the shoe. As will be readily understood, this arrangement increases the seating and the flexibility of the shoe to give the patient a good balance when walking.

According to another important feature of the invention, sole 4 is compressible, its degree of compressibility increasing from the rear to the front. To obtain this latter property, there is provided, in the upper part of the sole, a hard pad 6 of a decreasing thickness from the rear to the front, on which rests the inner sole 3 of the upper. The remaining part 7 of the sole having a longitudinal triangular cross section, is made from an homogeneous compressible material and more precisely from a cellular synthetic foam. Pad 6 and the compressible part 7 may be formed by two separate pieces joined to each other during manufacture of the shoe. Preferably, however, the sole is integrally molded from a synthetic resin, latex or rubber and according to a known process which allows partial cellular formation of the resin, latex or rubber.

It will be further noted here that, for reasons of protecting the compressible material, sole 4 comprises, on its walking surface, a plate 11 made from a hard material, this plate being possibly obtained by being integrally molded with the other parts of the sole.

Because of the variable compressibility of sole 4, sudden stopping of the support of the rear part of the foot is avoided at the front part of the shoe, which considerably improves the comfort of the patient when walking. Furthermore, the hard pad 6 forms an anti-shock protection for the foot.

The shoe of the invention further comprises, placed between the inner sole 3 of the upper and sole 4, a base 8 which extends beyond the front edge of the inner sole 3 of the upper by a flexible downwardly curved tongue 9. This flexible tongue allows partial folding of the foot during walking. Moreover, this tongue stops along a curve corresponding to the Lisfranc interline of foot P, thus leaving free the metatarsian structure which is thus not subjected to any stress.

The upper 1 of the shoe of the invention must be sufficiently rigid to participate in holding the foot in a sloping position. This is why its two quarters 2 are made from a strong cloth reinforced by a stiffening and are cut at a height sufficient for wrapping round the rear part of the patient's foot to above the peroneo-tibial malleoli.

As can be seen, the quarters 2 are provided with self-gripping fasteners 10 which allow the upper 1 to be closed about foot P. These fasteners 10 are three in number, one being disposed at the level of the malleoli, the second on the front part of the upper and the third in an intermediate position; they form an adjustable means for closing the upper depending on the size of the foot. More precisely, after a surgical operation on the fore-foot, they allow adjustment depending on the development of the post-operative oedema.

The shoe which has just been described is essentially used as a post-operative shoe for patients having undergone a surgical operation on the fore-foot, but may of course serve as footwear for patients suffering from a traumatic affection of the fore-foot.

In these uses, it offers the possibility to the patients who wear it of walking normally during their convalescence, without the help of crutches or sticks, and this even if they are compelled to wear a shoe on each foot.

We claim:

1. A shoe, especially for a patient having undergone a surgical operation on the fore-foot, comprising: an upper open at the front and adapted to wrap round a rear part of the foot while leaving the metatarsal heads of the foot free; and a compressible sole substantially thicker at the front than at the rear, arranged at and secured below the upper, and sized to also leave the metatarsal heads of the foot free, whereby the whole foot of the patient is maintained sloping and away from the ground during walking.

2. A shoe according to claim 1, wherein the sole forms a wedge.

3. A shoe according to claim 2, wherein the sole has a degree of compressibility increasing from the rear to the front.

4. A shoe according to claim 3, wherein the sole comprises a hard pad on which rests the upper, the remaining part of the sole being formed of a homogeneous compressible material.

5. A shoe according to claim 4, wherein said homogeneous compressible material is a cellular foam of latex, rubber or synthetic material.

6. A shoe according to claim 4 or 5, wherein the pad and the compressible part of the sole are integrally molded to each other.

7. A shoe according to any one of claims 1 to 3, wherein the upper comprises an inner sole resting on said sole, a base placed between the sole and the inner sole of the upper, said base having a flexibly downwardly curved tongue, extending beyond the front edge of the inner sole, said tongue stopping along a curve corresponding to the Lisfranc interline of the foot.

8. A sole according to any one of claims 1 to 3, wherein the upper comprises two quarters which are connected to each other so as to extend over the instep of the patient's foot, said quarters being made from a strong cloth and having a sufficient height to wrap around the rear part of the foot to above the peroneotibial malleoli.

9. A shoe according to claim 8, comprising self-gripping fasteners for connecting the two quarters of the upper to each other.

10. A shoe according to any one of claims 1 to 3, wherein the sole has a protection plate of a hard material on the walking surface thereof.

* * * * *